(12) United States Patent
Stultz et al.

(10) Patent No.: US 10,589,022 B2
(45) Date of Patent: Mar. 17, 2020

(54) SYRINGE PLUNGER POSITIONING APPARATUS AND METHOD

(71) Applicant: Baxter Corporation Englewood, Englewood, CO (US)

(72) Inventors: Tammy Stultz, Westminster, CO (US); Randall Wallace Smith, Lakewood, CO (US); Yuriy Konstantinovich Umanskiy, Centennial, CO (US)

(73) Assignee: Baxter Corporation Englewood, Englewood, CO (US)

( * ) Notice: Subject to any disclaimer, the term of this patent is extended or adjusted under 35 U.S.C. 154(b) by 816 days.

(21) Appl. No.: 14/984,285

(22) Filed: Dec. 30, 2015

(65) Prior Publication Data

US 2017/0189608 A1    Jul. 6, 2017

(51) Int. Cl.
*A61M 5/145*    (2006.01)
*A61M 5/178*    (2006.01)
*A61M 5/20*    (2006.01)

(52) U.S. Cl.
CPC ........ *A61M 5/1456* (2013.01); *A61M 5/1782* (2013.01); *A61M 5/20* (2013.01);
(Continued)

(58) Field of Classification Search
CPC .... A61M 5/1782; A61M 5/142; A61M 5/145; A61M 5/14566; A61M 5/1458; A61M 5/1456; A61M 2005/14573; A61M 2005/3114; A61M 5/178; A61M 5/20; A61M 5/14546; A61M 2005/2006; A61M 2205/3306; B65B 3/003; Y10T 24/44436;
(Continued)

(56) References Cited

U.S. PATENT DOCUMENTS 3,898,637 A    8/1975 Wolstenholme
4,599,888 A    7/1986 Hufton et al.
(Continued)

FOREIGN PATENT DOCUMENTS

EP    2301603 A1    3/2011
JP    2003127083 A    5/2003
(Continued)

*Primary Examiner* — Kevin C Sirmons
*Assistant Examiner* — Alexandra Lalonde
(74) *Attorney, Agent, or Firm* — K&L Gates LLP (57) ABSTRACT

An apparatus and method for syringe plunger positioning employing an actuator for linear advancement and retraction of the support member along a predetermined axis, and a plurality of arm members each interconnected to the support for movement therewith, and each moveable relative to the support member in corresponding different directions towards and away from the predetermined axis. The actuator may be operable to advance the support member to an advanced position for movement of the arm members from an open position to a closed position, and to retract the support member from the advanced position so that of the arm members engage an inside surface of a plunger button of syringe having a barrel located in a fixed, axially aligned position on the predetermined axis. The apparatus and method may be employed in conjunction with syringe plunger positioning (e.g. for filling operations) that accommodates a variety of syringe plunger configurations.

20 Claims, 8 Drawing Sheets

(52) U.S. Cl.
CPC ............. *A61M 2005/14573* (2013.01); *A61M 2005/2006* (2013.01); *A61M 2205/3306* (2013.01)

(58) Field of Classification Search
CPC .... Y10T 24/44291; A61J 1/20; G06F 11/027; G06F 11/00
See application file for complete search history.

(56) References Cited

U.S. PATENT DOCUMENTS

| | | | |
|---|---|---|---|
| 4,755,172 A | 7/1988 | Baldwin | |
| 5,775,755 A * | 7/1998 | Covert | B25J 15/0226 294/100 |
| 6,349,740 B1 | 2/2002 | Cho et al. | |
| 6,616,771 B2 | 9/2003 | Osborne et al. | |
| 6,722,404 B2 | 4/2004 | Osborne | |
| 6,813,868 B2 | 11/2004 | Baldwin et al. | |
| 6,877,530 B2 | 4/2005 | Osborne et al. | |
| 6,915,619 B2 | 7/2005 | Baldwin | |
| 6,915,823 B2 | 7/2005 | Osborne et al. | |
| 6,957,522 B2 | 10/2005 | Baldwin et al. | |
| 6,976,349 B2 | 12/2005 | Baldwin et al. | |
| 6,991,002 B2 | 1/2006 | Osborne et al. | |
| 7,017,622 B2 | 3/2006 | Osborne et al. | |
| 7,025,098 B2 | 4/2006 | Osborne | |
| 7,117,902 B2 | 10/2006 | Osborne | |
| 7,128,105 B2 | 10/2006 | Tribble et al. | |
| 7,207,152 B2 | 4/2007 | Baldwin | |
| 7,240,699 B2 | 7/2007 | Osborne et al. | |
| 7,377,148 B2 | 5/2008 | Cassidy et al. | |
| 7,392,638 B2 | 7/2008 | Baldwin et al. | |
| 7,403,125 B2 | 7/2008 | Rich | |
| 7,469,518 B2 | 12/2008 | Baldwin | |
| 7,478,513 B2 | 1/2009 | Baldwin | |
| 7,631,475 B2 | 12/2009 | Baldwin et al. | |
| 7,681,606 B2 | 3/2010 | Khan et al. | |
| 7,753,085 B2 | 7/2010 | Tribble et al. | |
| 7,892,210 B2 | 2/2011 | Ranalletta et al. | |
| 7,913,720 B2 | 3/2011 | Tribble et al. | |
| 7,997,304 B2 | 8/2011 | Ranalletta et al. | |
| 8,037,659 B2 | 10/2011 | Osborne et al. | |
| 8,191,339 B2 | 6/2012 | Tribble et al. | |
| 8,209,941 B2 | 7/2012 | Osborne et al. | |
| 8,220,503 B2 | 7/2012 | Tribble et al. | |
| 8,353,318 B2 | 1/2013 | Ranalletta et al. | |
| 8,489,341 B2 | 7/2013 | Brown | |
| 8,496,646 B2 | 7/2013 | Kamen et al. | |
| 8,678,047 B2 | 3/2014 | Tribble et al. | |
| 8,857,269 B2 | 10/2014 | Johnson et al. | |
| 8,863,788 B2 | 10/2014 | Ranalletta et al. | |
| 2005/0220639 A1 * | 10/2005 | Sasaki | A61M 5/1458 417/415 |
| 2007/0191770 A1 * | 8/2007 | Moberg | A61M 5/14566 604/131 |
| 2010/0160137 A1 | 6/2010 | Scibona et al. | |
| 2014/0142537 A1 | 5/2014 | Gibson et al. | |
| 2014/0171868 A1 | 6/2014 | Zhang et al. | |

FOREIGN PATENT DOCUMENTS

| | | |
|---|---|---|
| WO | 2005119181 A1 | 12/2005 |
| WO | 2015041092 A1 | 3/2015 |

* cited by examiner

SYRINGE PLUNGER POSITIONING APPARATUS AND METHOD

RELATED APPLICATIONS

This application relates to and incorporates by reference the co-owned application having Provisional Ser. No. 62/272,786 by Stultz et al. filed on Dec. 30, 2015 entitled SYRINGE POSITIONING APPARATUS AND METHOD. This application relates to and incorporates by reference the co-owned application having Provisional Ser. No. 62/272,789 by Umanskiy et al. filed on Dec. 30, 2015 entitled MEASUREMENT OF SYRINGE GRADUATION MARKS USING A VISION SYSTEM. This application relates to and incorporates by reference the co-owned application having Provisional Ser. No. 62/272,794 by Umanskiy et al. filed on Dec. 30, 2015 entitled CAPACITIVE SINGLE PLATE BUBBLE DETECTOR. This application relates to and incorporates by reference the co-owned application having application Ser. No. 14/984,022 by Ward et al. filed on Dec. 30, 2015 entitled SOURCE FLUID INLET ASSEMBLY FOR AUTOMATED FILLING DEVICE. This application relates to and incorporates by reference the co-owned application having Provisional Ser. No. 62/272,798 by Hutchison et al. filed on Dec. 30, 2015 entitled SYRINGE GRIPPING APPARATUS AND METHOD. This application relates to and incorporates by reference the co-owned application having Provisional Ser. No. 62/272,816 by Ward et al. filed on Dec. 30, 2015 entitled INLET TUBE SET FOR SOURCE INGREDIENT DELIVERY. This application relates to and incorporates by reference the co-owned application by Stultz et al. filed on Dec. 30, 2015 entitled TIP CAP FOR AUTOMATIC SYRINGE FILING APPARATUS.

BACKGROUND

Syringes are employed to dispense a variety of flowable materials, including therapeutic, diagnostic and other materials utilized in medical applications. In that regard, it is typical to utilize a syringe of a size that generally corresponds with a predetermined amount of material to be dispensed or to otherwise be available for dispensation in a given procedure. For example, in medical applications such amount may be established pursuant to prescription or industry practice, and may significantly vary depending upon the given intended use. In turn, a wide range of syringe sizes are utilized by medical care providers.

Until recently, syringe filling was largely completed manually. In medical applications, such manual filling has typically been completed in pharmacies by highly-trained personnel, including pharmacies located at patient care provider sites having space constraints (e.g. a hospital pharmacy).

Increasingly, attempts have been made to automate one or more steps associated with syringe filling. Such automation may be desirable for a number of reasons, including for example cost efficiencies and quality control. However, such attempts have confronted a number of challenges.

In particular, automated systems typically require automated positioning of syringe plungers with a high degree of accuracy, on a repeatable and reliable basis. To address such requirements, known automated systems have utilized complex componentry that has restricted the ability to efficiently handle syringes of different sizes and configurations, including in particular, syringes having different plunger button configurations. Further, in typical medical-related applications, syringe handling may necessarily require a sterile environment that often entails the use of a vented enclosure, thereby further compounding space constraints in typical pharmacy settings.

SUMMARY

The present disclosure addresses the above-noted challenges to provide improved apparatus and methods for automated syringe plunger positioning.

In disclosed embodiments, a syringe plunger positioning apparatus is disclosed that includes an actuator to linearly advance and retract a support member along a predetermined axis in an automated manner. The apparatus may further include a plurality of arm members, each interconnected to the support member for movement therewith, and each moveable relative to the support member in corresponding different directions towards the predetermined axis. The actuator may be operable to advance the support member to an advanced position for movement of the plurality of arm members in different corresponding directions towards the predetermined axis (e.g. from an open position to a closed position). Further, the actuator may be operable to retract the support member from the advanced position so that distal end portions of each of the plurality of arm members may engage and apply a retraction force to an inside surface of a plunger button of a syringe having a barrel located at a fixed, axially aligned position on the predetermined axis, thereby retracting a plunger relative to the barrel of the syringe (e.g. for syringe filling). The apparatus may also include a controller to control the actuator for advancement and retraction of the support member in an automated manner.

As may be appreciated, the utilization of an actuator to advance a support member to an advanced position for movement of a plurality of arm members in corresponding different directions toward a predetermined axis to a closed position, and to retract the support member from the advanced position to cause distal end portions of the arm members to engage and apply a retraction force to an inside surface of a plunger button of a syringe, facilitates automated syringe plunger positioning of syringes having a wide range of plunger button configurations (e.g. plunger buttons having cross-dimensions from about 10 mm to about 35 mm). In turn, the disclosed syringe plunger positioning apparatus may be employed with a wide variety of syringes in conjunction with filling operations and other procedures entailing plunger positioning.

In contemplated embodiments, the syringe plunger positioning apparatus may include a contact member interconnected to the support member for movement therewith. The contact member may be located and moveable relative to the support member along the predetermined axis so that, upon advancement of the support member to the advanced position by the actuator, the contact member is engageable with and displaceable rearwardly from a forward position to a rearward position, relative to the support member, along the predetermined axis via contact engagement with an outside surface of a plunger button of a syringe having a barrel located in a fixed, axially aligned position on the predetermined axis.

In some embodiments, the contact member may be provided so that, upon retraction of the support member from the advanced position by the actuator, the contact member is automatically moved forward from the rearward position to a stop position, relative to the support member, contemporaneous with retraction of the distal end portions of the plurality of arm members in to engagement with an inside surface of a plunger button of a syringe having a barrel located in a fixed axially aligned position on the predetermined axis. In some arrangements, the contact member may be biased to the forward position (e.g. by a spring member), wherein a biasing force is applied to the contact member to facilitate automatic forward movement of the contact member from a rearward position to a stop position, relative to the support member. Further, such biasing force may be translated to the outside surface of a plunger button engaged by the contact member, in opposing relation to a greater retraction force applied to an inside surface of the plunger button by the distal end portion of the arm members, wherein plunger button positioning may be precisely controlled during retraction of the support member to a retracted position.

The apparatus may further include a sensor for sensing movement of the contact member from the rearward position to the stop position, relative to the support member, and for providing a sensor output indicative thereof. Advantageously, the sensor output may be employable to control the actuator to retract the support member to a retracted position that is a predetermined draw distance along the predetermined axis from a position of the support member that corresponds with sensing of the advancement of the contact member to the forward position relative to the support member.

In that regard, the predetermined draw distance may correspond with a desired, predetermined magnitude of syringe filling with a flowable material. By way of example, the desired, predetermined magnitude of syringe filling may correspond with a specific volume of flowable material and/or a specified graduation on a syringe barrel indicative of a corresponding volume of flowable material.

In some implementations, the above-noted sensor may comprise a capacitive sensor that includes spaced first and second conductive surfaces. In some implementations, the first and second conductive surfaces may be disposed in substantially parallel, spaced planes. The first conductive surface may be supported by and in fixed relation to the support member, and the second conductive surface may be supported by and in fixed relation to the contact member, wherein the capacitive sensor is operable to sense an electrical capacitance between the first and second conductive surfaces and provide an output indicative thereof.

In turn, when the actuator retracts the support member from the advanced position and the contact member is automatically and contemporaneously moved from the rearward position to the stop position, relative to the support member, as described above, the capacitive sensor will sense a marked change in capacitance and a continuing change in capacitance until the contact member reaches the stop position, at which time the capacitance will stop changing. In turn, a processor may process the output to determine when the contact member has reached the stop position (e.g. when the rate of change of the sensed capacitance drops below a predetermined or predeterminable level), whereupon a controller may control the actuator to retract the support member to a retracted position that is a predetermined draw distance along the predetermined axis from a position of the support member that corresponds with sensing movement of the contact member to the stop position relative to the support member. By way of example, the processor may process the sensor output to determine when the rate of change of the sensed capacitance drops below a predetermined or predeterminable level (e.g. thereby indicating that the contact member has reached the stop position), and to provide a corresponding indication for use by the controller in controlling actuator retraction to the retracted position.

In some embodiments, the capacitive sensor may be provided so that when the carrier member is in the forward position relative to the support member, the first conductive surface and second conductive surface are disposed in overlapping relation, and so that when the contact member is retracted rearward of the forward position, relative to the support member, the first and second conductive surfaces are disposed in increasingly non-overlapping relation. In other arrangements, the capacitive sensor may be provided so that when the carrier member is in the forward position relative to the single support member, the first conductive surface and second conductive surface are disposed in non-overlapping relation, and so that when the contact member is retracted rearward of the forward position, relative to the support member, the first and second conductive surfaces are disposed in increasingly overlapping relation.

The use of a capacitive sensor is just one approach for distance change determination (i.e. the distance traveled form the rearward position to the stop position by the contact member). In other embodiments, the sensor for sensing movement of the contact member from the rearward position to the stop position may comprise a reflective optical sensor, an ultrasound sensor, a linear variable differential transformer sensor, or other sensors capable of such sensing.

In some embodiments, the actuator may comprise an electric motor (e.g. a stepper motor), wherein the controller may control the motor operating for support member positioning (e.g. to control a number of motor steps of a stepper motor where each step corresponds with a predetermined distance of support member advancement or retraction). In turn, the controller may be operable to automatically control operation of the motor to advance the support member to the desired advanced position, and to automatically control operation of the motor to retract the support member from the advanced position to the retracted position utilizing the sensor output (e.g. the capacitive sensor output) and motor control data corresponding with the predetermined draw distance noted above. In some implementations, the controller may be operable to automatically control operation of the motor to retract the support member from the advanced position to the retracted position in a continuous motion.

In contemplated embodiments, the actuator may further comprise a linear actuator extending along the predetermined axis and operatively interconnected to an output shaft of the motor and to the support member for driven movement of the support member along the predetermined axis upon operation of the motor. By way of example, the linear actuator may comprise a lead screw/nut arrangement, wherein one end of the lead screw is interconnected to an output shaft of the motor for driven rotation, and wherein the nut is fixedly interconnected to the support member for driven advancement and retraction along the predetermined axis. As may be appreciated, in such arrangements, the lead screw may be disposed to extend in parallel relation to the predetermined axis.

In some implementations, the syringe plunger positioning apparatus may include a sensor for sensing positioning of the support member in a predetermined home location and for providing a sensor output indicative thereof to the controller. In turn, the controller may be operable to automatically control the motor to advance the support member a predetermined positioning distance along the predetermined axis from the predetermined home location to the advanced position. In one approach, the sensor may include an optical sensor fixedly positioned relative to one end of the linear actuator and a flag member interconnected to the support member for movement therewith, wherein when the support member is located in the predetermined home location the optical sensor senses the presence of the flag member.

The predetermined positioning distance noted above may be established in relation to a predetermined location range of a button of a plunger of a syringe having a barrel supportably located at a fixed, axially aligned position on the predetermined axis AA. By way of example, such predetermined location range may be based upon positioning of a dispensing end of a given syringe at a predetermined location, or reference datum, on the predetermined axis, and further based upon predetermined data stored at the controller relating to a length of the syringe barrel of the given syringe.

In some embodiments, the plurality of arm members are each moveable for synchronous advancement of the corresponding distal end portions toward the predetermined axis. Further, the arm members may each be moveable so that their corresponding distal end portions follow corresponding different arcuate paths toward the predetermined axis. In that regard, the plurality of arm members may be provided so that each of the arcuate paths extend about a periphery of a plunger button of a syringe located on the predetermined axis and toward the predetermined axis, when the support member is at or is advanced to the advanced position.

In contemplated arrangements, each of the plurality of arm members may be pivotally interconnected to a housing that is fixedly interconnected to an upstanding portion of the support member. More particularly, the plurality of arm members may comprise two arm members disposed for pivotal movement towards and away from the predetermined axis on opposing sides thereof. In some embodiments, the two arm members may be disposed for pivotal movement in a plane in which the predetermined axis extends. In turn, upon a movement of the arm members toward the predetermined axis to a closed position and retraction of the support member, the distal end portions of the two arm members may be located so as to engage the inside surface of a plunger button of a syringe positioned on the predetermined axis at substantially aligned locations on opposing sides of the predetermined axis.

In some implementations, the plurality of arm members may each be biased to a closed position relative to the predetermined axis. By way of example, each of the arm members may be biased by a corresponding torsion spring.

In conjunction with some embodiments, the syringe plunger positioning apparatus may include an activatable device (e.g. an electrically-activatable device such as a solenoid) having an end portion extending from the housing and selectively displaceable upon activation of the device to engage the plurality of arm members and thereby pivot the plurality of arm members (e.g. against the above-noted biasing) from the closed position to an open position relative to the predetermined axis. In turn, a controller may be provided to automatically control activation and deactivation of the device, wherein the device may be activated to locate the arm members in an open position during all or at least a position of the advancement of the support member to the advanced position, and deactivated when the support member is approaching and/or otherwise located at the advanced position.

In some implementations, the plurality of arm members may each define a U-shaped configuration along a length thereof. In that regard, each of the arm members may include first and second portions defining an included angle therebetween. In contemplated arrangements, the included angle may be between about 9° to about 75°.

In some implementations, the distal end portions of the plurality arm members may each comprise reduced ends that taper toward the support member when the arms are biased to the closed position relative to the predetermined axis. In that regard, the reduced ends may be provided to facilitate non-slip, contact engagement with the inside surface of a plunger button of a syringe located in an axially aligned position on the predetermined axis.

In further embodiments, an automated syringe plunger positioning method is disclosed that comprises advancing a support member and a plurality of arm members interconnected thereto along a predetermined axis to an advanced position relative to a syringe having a barrel in a fixed, axially aligned position on the predetermined axis. Such embodiments may further include moving each of the arm members in corresponding different directions towards the predetermined axis from an open position to a closed position. Further, method embodiments may include retracting the support member and interconnected arm members from the advanced position so that distal end portions of the plurality of arm members engage and apply a retraction force to an inside surface of a plunger button of the syringe to retract a plunger from the syringe barrel.

In some implementations, method embodiments may further include locating the arm members in the open position prior to advancement of the support member and arm members to the advanced position. By way of example, such locating may be completed prior to the advancing step or during the advancing in sufficient time to accommodate passage of the arm members about the periphery of the syringe button of the given syringe located on the predetermined axis.

In some embodiments, the arm members may be biased towards the closed position, and the locating step may comprise activating an activatable device to engage and thereby move the arm members away from the predetermined axis to the open position. In turn, such embodiments may further comprise maintaining activation of the activatable device during at least a portion of the advancing step. Further, the moving step may include deactivating the activatable device to disengage the activatable device from the arm members for biased movement of the arm members to the closed position.

In contemplated arrangements, the advancing step may include controlling an actuator to advance the support member a predetermined positioning distance from a predetermined home location. The predetermined positioning distance may be established in relation to a predetermined location range of a button of a plunger of a syringe having a barrel supportably located at a fixed, axially aligned position on the predetermined axis AA. By way of example, such predetermined location range may be based upon positioning of a dispensing end of a given syringe at a predetermined location, or reference datum, on the predetermined axis, and further based upon predetermined data stored at the controller relating to a length of the syringe barrel of the given syringe.

In such embodiments, the method may further comprise sensing the positioning of the support member at the home location and providing a sensor output responsive thereto prior to the controlling step. As may be appreciated, the sensor output may be utilized by a controller to confirm that the support member is at the predetermined home location, whereupon the controller may initiate the controlling step.

In some implementations, the moving step may include pivoting the arm members relative to the support member, wherein the distal end portions of the arm members move along corresponding arcuate paths towards the predetermined axis to the closed position. In that regard, each of the arm members may be pivotally interconnected to a housing that is interconnected to an upstanding portion of the support member.

In contemplated embodiments, the retracting step may comprise retracting the support member a predetermined draw distance from a position of the support member when the distal end portions of the arm members engage the inside surface of the plunger button. In that regard, the predetermined draw distance may correspond with a desired, predetermined magnitude of syringe filling with a flowable material. By way of example, the desired, predetermined magnitude of syringe filling may correspond with a specific volume of flowable material and/or a specified graduation on a syringe barrel indicative of a corresponding volume of flowable material.

In conjunction with such embodiments, the method may further include displacing a contact member supported by the support member from a forward position to a stop position, relative to the support member, by engagement of the contact member with an outside surface of the plunger button during an end portion of the advancing step. In turn, such embodiments may further include moving the contact member forwardly from the rearward position to a stop position, relative to the support member, contemporaneous with retraction of the distal end portions of the support arms into engagement with the inside surface of the plunger button. In that regard, the contact member may be biased to the forward position, wherein the moving step may include applying automatically a biasing force to the contact member.

In conjunction with such embodiments, the method may further include sensing the movement of the contact member from the rearward position to the stop position, relative to the support member. In one approach, the sensing step may include sensing an electrical capacitance between a first conductive surface located on and in fixed relation to the support member and a second conductive surface located on and in fixed relation to the contact member, and providing a sensor output indicative of the sensed capacitance. In turn, such embodiments may further include processing the output to determine when a rate of change of the sensed capacitance drops below a predetermined or predeterminable level, whereupon the actuator is controlled to retract the support member a predetermined draw distance. As noted above, the predetermined draw distance may correspond with a predetermined magnitude of syringe filling with a flowable material.

Additional features and advantages of the present invention will become apparent upon consideration of the description that follows.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular application(s) or use(s) of the present invention.

Figure 1A:
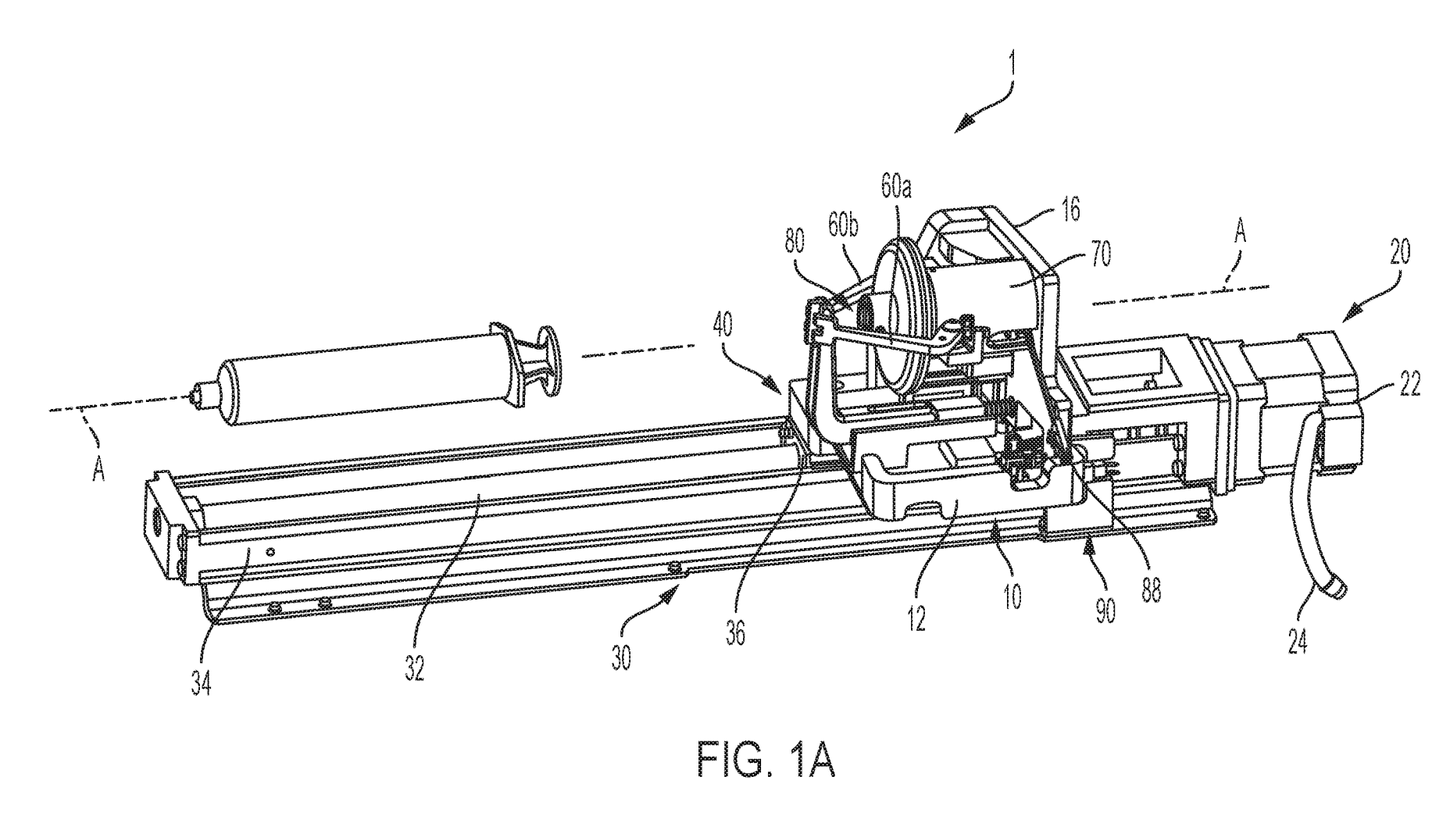
FIG. 1A is a perspective view of one embodiment of a syringe plunger positioning apparatus.
Figure 1B:
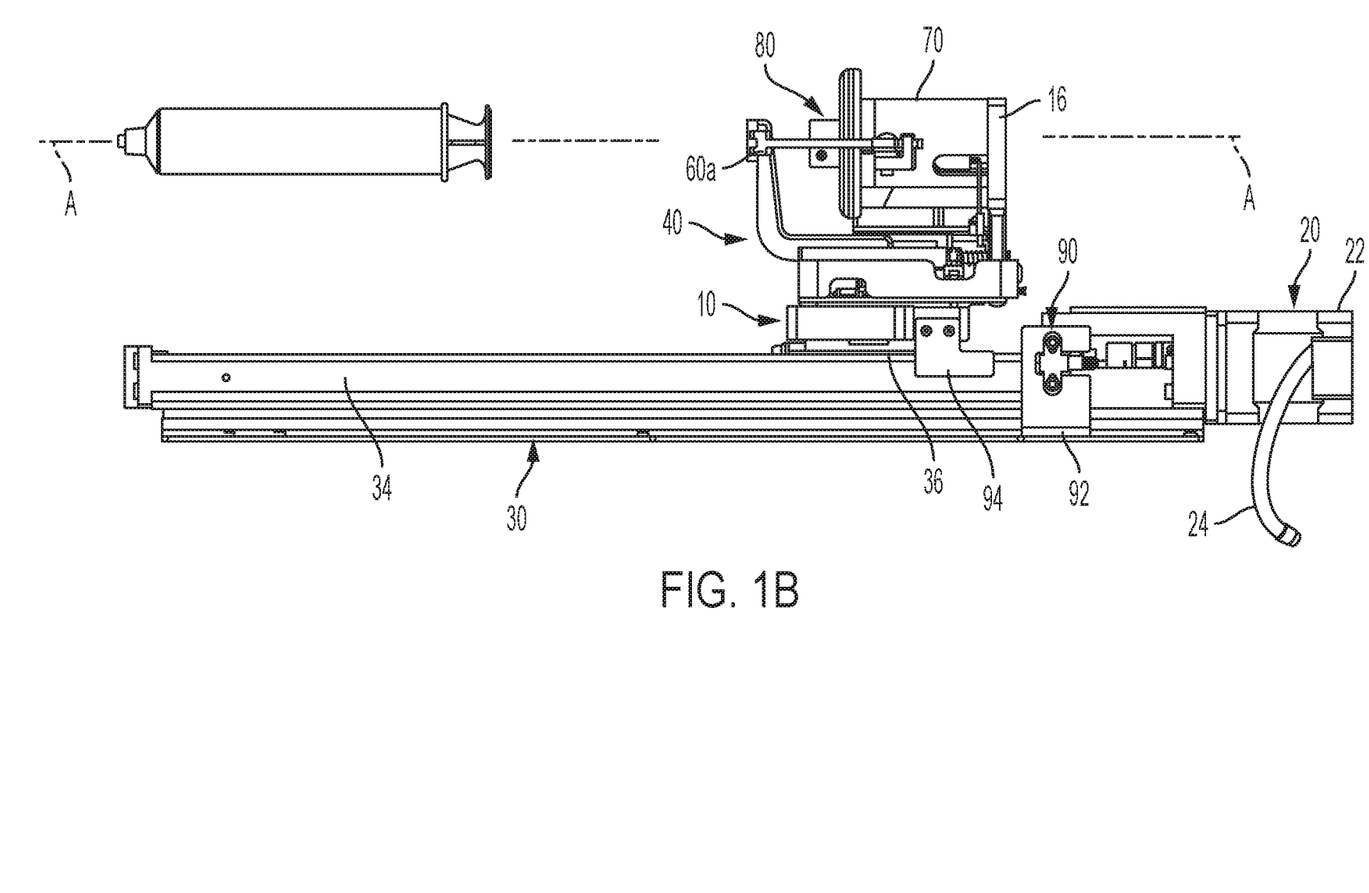
FIG. 1B is a side view of the syringe plunger positioning apparatus embodiment of FIG. 1A.

One embodiment of a syringe plunger positioning apparatus (1) is shown in FIGS. 1A and 1B and includes a support member (10) and two arm members (60a), (60b) supportably interconnected to the support member (10). The syringe plunger positioning apparatus (1) may further include an actuator (20) to linearly advance and retract the support member (10) along a predetermined axis AA so as to position the arm members (60a), (60b) for movement in different corresponding directions towards and away from the predetermined axis AA, and for distal end engagement with a button end of a plunger of a syringe having a barrel supportably located at a fixed, axially aligned position on the predetermined axis AA, as will be further described.

The actuator (20) may comprise an electric motor (22) (e.g. a stepper motor) having an output shaft operatively interconnected to a linear actuator (30). The linear actuator (30) may be of a lead screw/nut configuration, wherein one end of a lead screw (32) may be fixedly interconnected to an output shaft of the motor (22) and a second end of the lead screw (32) may be journaled for rotation at an end plate of a linear actuator housing (34). In turn, the linear actuator (30) may further include a nut member (36) in threaded engagement with lead screw (32) and fixedly interconnected to a base portion (12) of the support member (10). In turn, motor (22) may be operated to rotate the output shaft in a first direction to rotate lead screw (36) and advance the support member (10) towards a syringe having a barrel located at a fixed, axially aligned position on the predetermined axis AA, and motor (22) may be operated to rotate the output shaft in a second direction to rotate lead screw (32) and retract the support member (10) away from the barrel of syringe. As shown, motor (22) may include at least one connector (24) for interconnection to and receiving control signals from a controller.

In that regard, the syringe plunger positioning apparatus (1) may include one or more controller(s) to control operation of the actuator (20) and other automated components. By way of example, such controller(s) may comprise one or more microprocessors configurable to execute preprogrammed instructions (e.g. stored in non-transitory memory) and to utilize stored, input or sensed data (e.g. stored in transitory and/or non-transitory memory) to provide control signals to the motor (22) and/or other automated components, as will be further described. By way of example, when motor (22) comprises a stepper motor, the controller(s) may control a number of motor steps, where each motor step corresponds with a predetermined distance of advancement or retraction of support member (10).

In the illustrated embodiment, the arm members (60a), (60b) may be interconnected to the support member (10) via a housing (70) that is interconnected to and extends forwardly from an upstanding portion (16) of the support member (10). The arm members (60a), (60b) may be pivotally interconnected to opposing sides of the housing (70) for selective movement of the arm members (60a), (60b) towards the predetermined axis AA to a closed position, and away from the predetermined axis AA to an open position. The arm members (60a), (60b) may include distal end portions for engagement with an inside surface of plunger button of a syringe having a barrel supportably located at a fixed, axially aligned position on the predetermined axis AA, as will be further described.

Syringe positioning apparatus (1) may further include a contact member (40) interconnected to the support member (10) for movement therewith, and moveable relative to the support member (10). The contact member (40) may include an upstanding post portion (42) having a contact face (42a) for contacting an outside surface of plunger button of a syringe having a barrel supportably located at a fixed, axially aligned position on the predetermined axis AA, as will be further described.

Figure 2A:
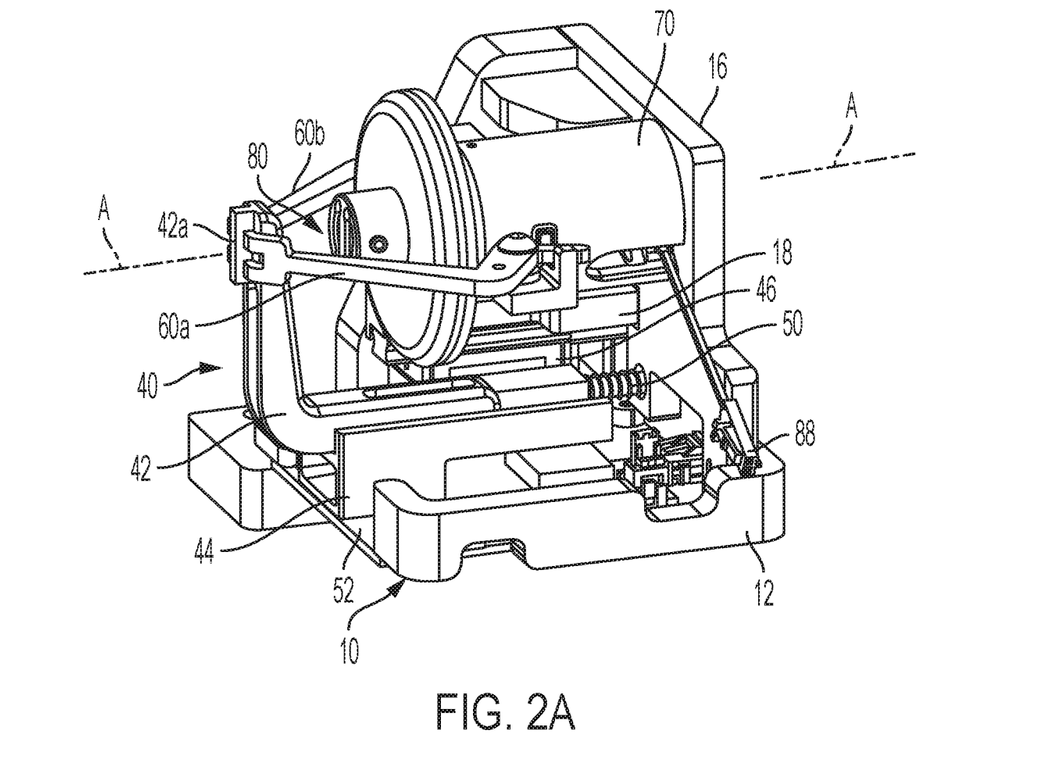
FIG. 2A is a perspective view of a support member and interconnected components of the syringe plunger positioning apparatus embodiment of FIG. 1A.
Figure 2B:
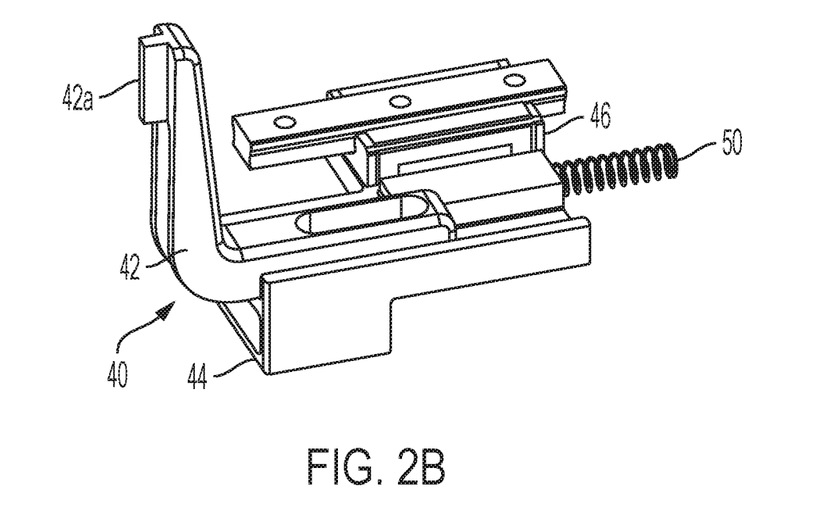
FIG. 2B is a perspective view of a contact member interconnected to the support member illustrated in FIG. 2A.
Figure 2C:
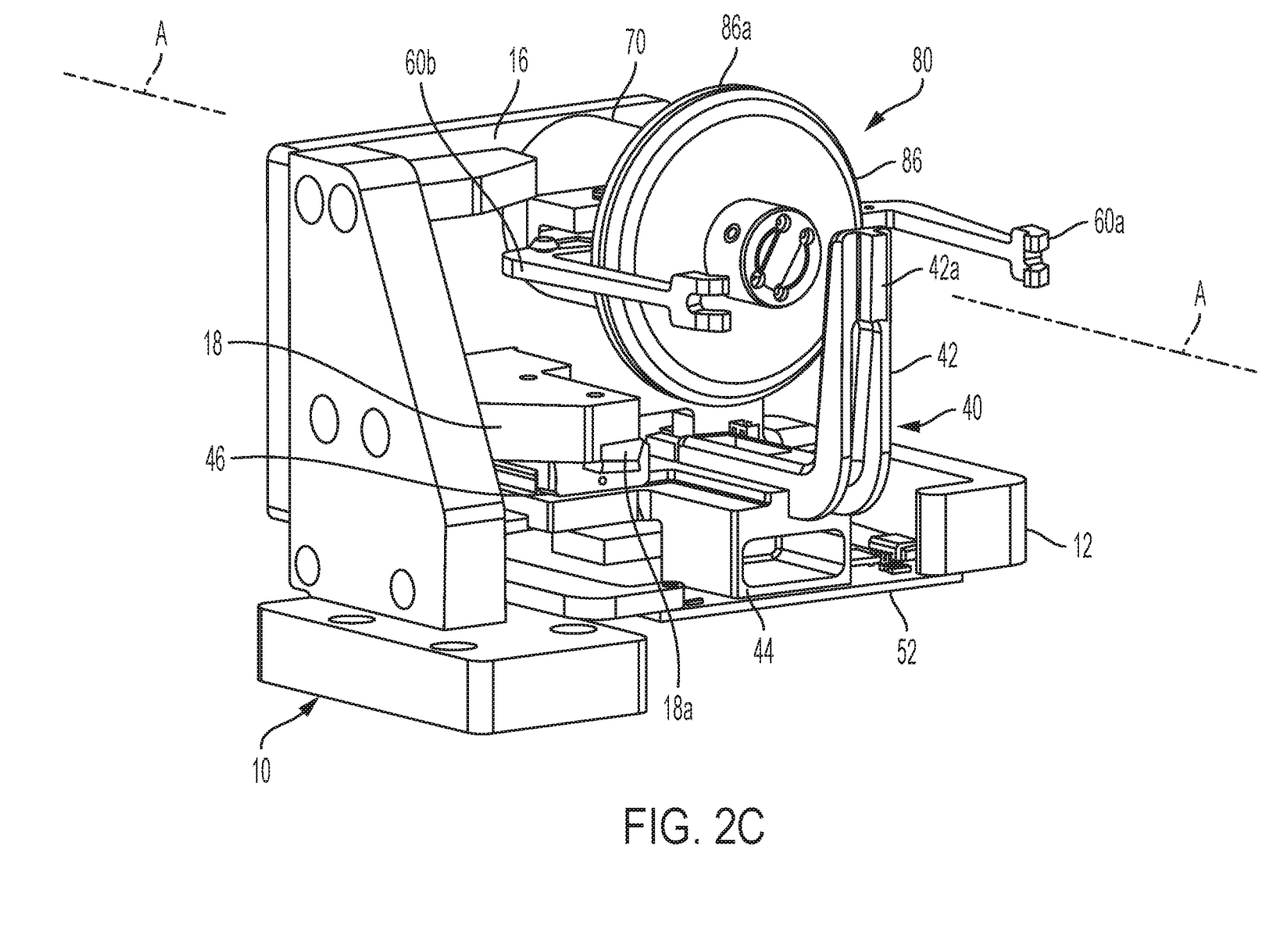
FIG. 2C is another perspective view of the support member and interconnected components illustrated in FIG. 2A.

Reference is now made to FIGS. 2A, 2B and 2C, which illustrate the interface between contact member (40) and support member (10). As shown, the contact member (40) may include a carrier portion (44) that is adjoined to the post portion (42) and to a guide portion (46). The guide portion (46) is slideably interconnected to and supported by the support member (10), wherein the contact member (40) is moveable linearly along the predetermined axis AA relative to the support member (10). As best shown in FIG. 2C, the guide portion (46) may be slideably supported on a rail (18a) provided under a shelf portion (18) of the support member (10) that projects forwardly from the upstanding portion (16), wherein the contact member (40) is suspended in spaced relation over the base portion (12) of the support member (10). As shown in FIGS. 2A and 2B, the syringe plunger positioning apparatus (1) may further include a spring member (50) interposed between upstanding portion (16) of the support member (10) and the carrier portion (44) of the contact member (40) so as to bias the contact member (40) to a forward position relative to the support member (10).

As shown in FIGS. 2A and 2C, the base portion (12) of support member (10) may support a substrate (52) on which electrical components and circuitry may be mounted. In particular, capacitive sensor componentry may be mounted on substrate (52), including an upward-facing, first conductive surface located in fixed relation to the support member (10). In turn, a downward-facing, second conductive surface may be located on a bottom side of and in fixed relation to the carrier portion (44) of the contact member (40), in spaced relation to the first conductive surface. The first and second conductive surfaces may be disposed in substantially parallel relation. Further, the first and second conductive surfaces may be disposed in overlapping, face-to-face, relation when the contact member (40) is located in the forward position, as noted above, and in increasingly, non-overlapping relation when the contact member (40) is moved rearwardly from the forward position relative to the support member (10).

The capacitive sensor may be provided to sense the magnitude of an electrical capacitance between the first and second conductive surfaces and to provide an output indicative thereof. In turn, such output may be employed in conjunction with control of the operation of the motor (22), as will be further described.

Figure 3A:
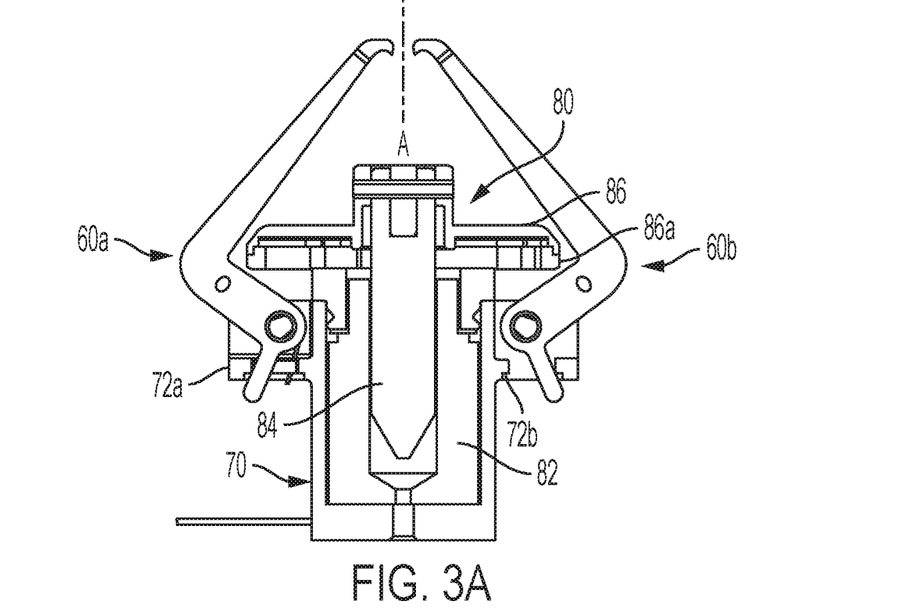
FIGS. 3A and 3B are top cross-sectional views of an activatable device of the syringe plunger positioning apparatus of FIG. 1, with arm members shown in closed and open positions, respectively.
Figure 3B:
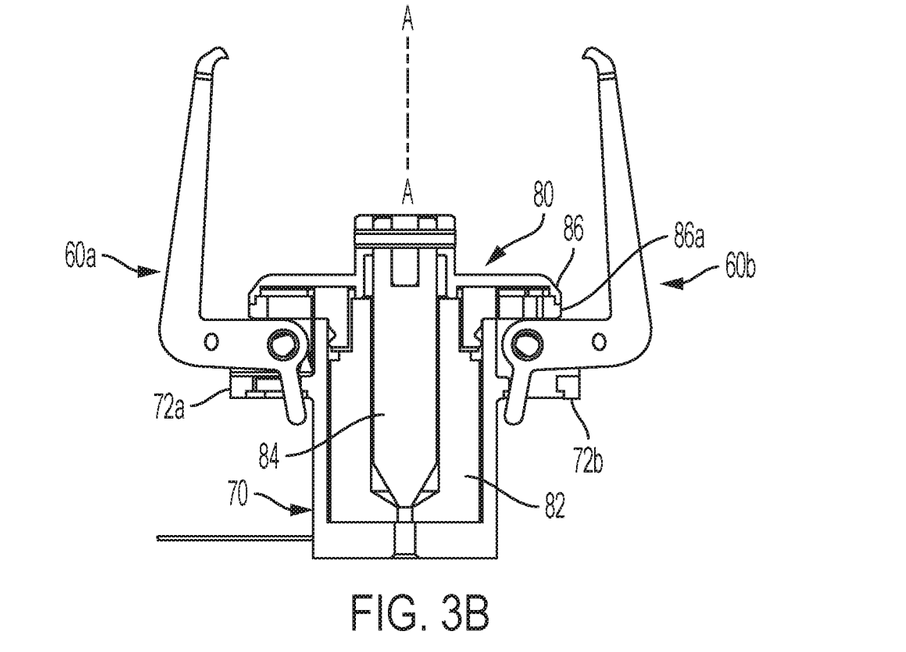

Reference is now made to FIGS. 3A and 3B, which further illustrate arm members (60a), (60b) pivotally interconnected to housing (70) on opposing sides thereof. For such purpose, housing (70) may include side projections (72a), (72b) to which first and second arm members (60a), (60b), may be pivotally interconnected (e.g. via a hinge/hinge pin arrangements), respectively.

As shown in FIG. 3A, the first and second arms (60a), (60b) may be biased to a closed position. By way of example, torsion spring members may be provided at each of the projections (72a) (72b) to interface with the arm members (60a), (60b) so as to urge the first and second arm members (60a), (60b) towards the predetermined axis AA to a closed position.

As shown in FIG. 3B, the syringe plunger positioning apparatus (1) may further include an electrically-activatable device (80) to selectively engage the arm members (60a), (60b) so as to move the arm members (60a), (60b) away from the predetermined axis AA to an open position. In the illustrated embodiment, the activatable device (80) may comprise a solenoid (82) and solenoid plunger (84) disposed in the housing (70). In turn, a forward end of a solenoid plunger (84) may be interconnected to an enlarged end (86) located forward of the housing (70). By way of example, the enlarged end (86) may be of a disc-shaped configuration and may be provided with a contact portion (86a) for engagement with the support members (60a), (60b). In the illustrated embodiment, the contact portion (86a) may be defined by a removable/replaceable member (e.g. a nylon member).

To advance the enlarged end (86) from a forward position illustrated in FIG. 3A to a rearward position illustrated in FIG. 3B, an electrical control signal may be provided by a controller to the solenoid (82) so as to magnetically induce movement of the solenoid plunger (84) rearwardly, and thereby effect contact engagement between the contact portion (86a) of the enlarged end (86) and each of the arm members (60a), (60b). As may be appreciated, upon deactivation of the activatable device (80), first and second arm members (60a), (60b) may be biased for movement from the open position back towards the predetermined axis AA to a closed position. As shown, activatable device (80) may include at least one connector (88) for interconnection to and receiving control signals from a controller.

To further describe operation of the syringe plunger positioning apparatus (1), reference is again made to FIGS. 1A and 1B. In FIG. 1A, support member (10) is shown in a predetermined home location. In FIG. 1B, support member (10) is shown in a position slightly advanced from the predetermined home location. As shown in FIG. 1B, the syringe plunger positioning apparatus (1) may further include a sensor (90) located to sense positioning of the support member (10) at the predetermined home location, as shown in FIG. 1A, and to provide a corresponding sensor output to a controller. More particularly, sensor (90) may include an optical sensor (92) interconnected to the linear actuator (30) at a location immediately adjacent to the predetermined home location. In turn, a flag member (94) may be interconnected to the support member (10) for movement therewith. Flag member (94) and optical sensor (92) may be provided so that when the support member (10) is in the predetermined home location, optical sensor (92) detects the presence of flag member (94) and provides a sensor output to a controller.

In typical operations, one or more controller(s) may activate the activatable device (80) to move the arm members (60*a*), (60*b*) to an open position, and to control the motor (22) to advance the support member (10) a predetermined positioning distance along the predetermined axis AA from the predetermined home location to an advanced location. The predetermined positioning distance may be established in relation to a predetermined location range of a button of a plunger of a syringe having a barrel supportably located at a fixed, axially aligned position on the predetermined axis AA. By way of example, such predetermined location range may be based upon positioning of a dispensing end of a given syringe at a predetermined location, or reference datum, on the predetermined axis, and further based upon predetermined data stored at the controller relating to a length of the syringe barrel of the given syringe.

As may be appreciated, a syringe may be located with a barrel supportably located at a fixed, axially-aligned position on the predetermined axis AA, and with a dispensing end of the syringe at a predetermined location, or reference datum, in any appropriate manner, and utilization of the syringe plunger positioning apparatus (1) is not restricted to any specific syringe positioning apparatus configurations. In one approach, a syringe may be positioned and a barrel of the syringe may be gripped for positioning of a dispensing end at a predetermined location, or referenced datum, along the predetermined axis AA utilizing syringe positioning and syringe gripping apparatus disclosed in co-filed U.S. Provisional Applications entitled "SYRINGE GRIPPING APPARATUS AND METHOD" and "SYRINGE POSITIONING APPARATUS AND METHOD", the entirety of which is herein incorporated by reference.

Figure 4A:
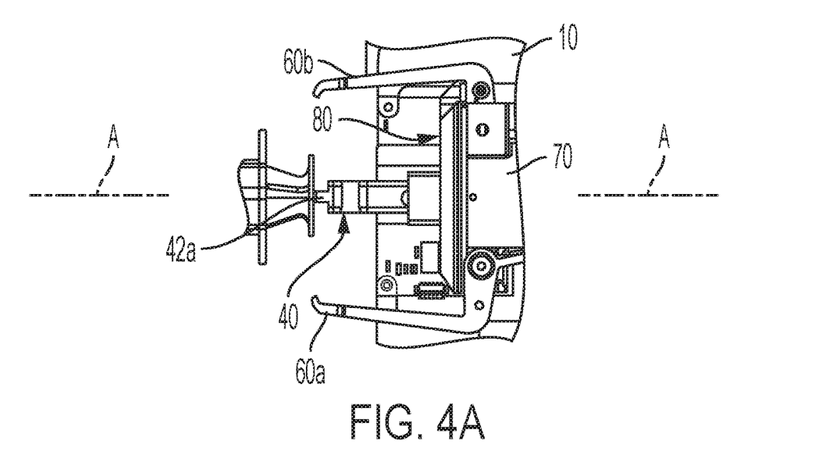
FIGS. 4A, 4B and 4C are top views illustrating progressive steps in positioning the syringe plunger positioning apparatus embodiment of FIG. 1A for engagement with a plunger button of a syringe
Figure 4B:
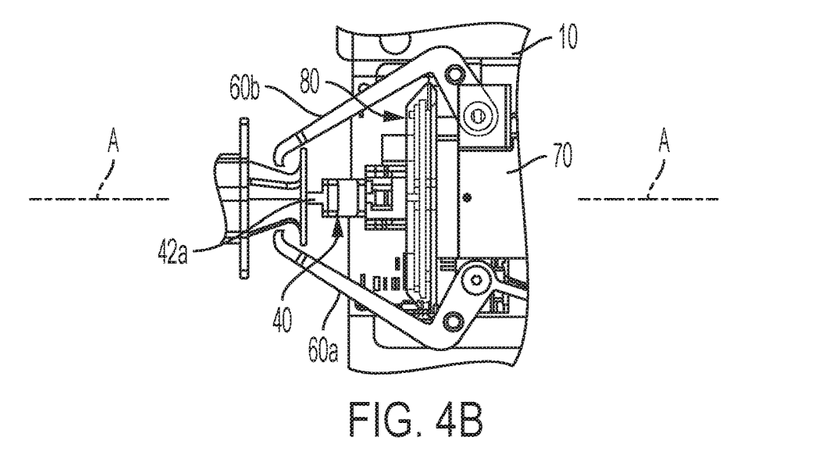
Figure 4C:
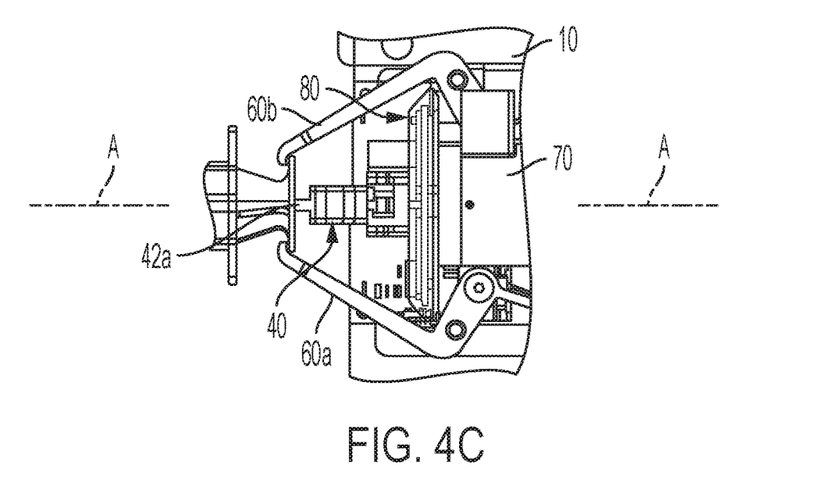

Reference is now made to FIGS. 4A, 4B and 4C which illustrate progressive steps of syringe plunger positioning utilizing the syringe plunger positioning apparatus (1). In FIG. 4A, motor (22) has been controlled by a controller to advance support member (10), contact member (40) and arm members (60*a*), (60*b*) towards a syringe located on the predetermined axis AA, with the contact surface (42*a*) of the contact member (40) initially engaging an outside surface of a plunger button of the syringe. As shown, activatable device (80) has been activated by a controller so as to locate arm members (60*a*), (60*b*) in an open position.

In turn, in FIG. 4B motor (22) has been further controlled by a controller to advance the support member (10), contact member (40) and arm members (60*a*) to an advanced position, relative to the syringe, with the contact member (40) forcibly displaced rearwardly against the biasing force applied to contact member (40) by spring member (50) to a retracted position, relative to the support member (10), by virtue of engagement with the outside surface of the plunger button. As will be appreciated, the biasing force applied by spring member (50) serves to maintain positive engagement between the contact member (40) and the outside of the plunger button. As further illustrated, in advancing from the position illustrated in FIG. 4A to the advanced position illustrated in FIG. 4B, activatable device (80) has been deactivated by a controller so that biased arm members (60*a*), (60*b*) have moved in corresponding different directions toward the predetermined axis AA to a closed position, wherein distal end portions of the arm members (60*a*), (60*b*) are located an offset distance from the inside surface of the plunger button.

In FIG. 4C, motor (22) has been further controlled by a controller to initiate retraction of the support member (10) and arm members (60*a*), (60*b*) a distance equal to the above-noted offset distance, i.e. to a position at which the distal end portions of the arm member (60*a*), (60*b*) have just engaged the inside surface of the plunger button. In conjunction with such retraction, the carrier member (40) has moved, from the rearward position to a stop position relative to the support member (10), in response to the biasing force applied by spring member (50). In conjunction with movement of the contact member (40) to the stop position, the capacitive sensor discussed above may provide a sensor output, whereupon a controller may further control the motor (22) to continue retraction of the support member (10) to a retracted position that is a predetermined draw distance along the predetermined axis AA from the position of the support member (10) shown in FIG. 4C so as to draw a desired, predetermined magnitude of flowable material into the barrel of the syringe.

More particularly, when the motor (22) is controlled to retract support member (10) from the advanced position and the contact member (40) is automatically and contemporaneously moved from the rearward position to the stop position, relative to the support member, the capacitive sensor will sense a marked change in capacitance and a continuing change in capacitance until the contact member (40) reaches the stop position, at which time the capacitance will stop changing. In turn, a processor of or interconnected to a controller may process the output to determine when the contact member (40) has reached the stop position (e.g. when the rate of change of the sensed capacitance drops below a predetermined or predeterminable level), whereupon a controller may control the motor (22) to retract the support member (10) to a retracted position that is a predetermined draw distance along the predetermined axis from a position of the support member (10) that corresponds with sensing movement of the contact member (40) to the stop position relative to the support member (10). By way of example, a processor may process the sensor output to determine when the rate of change of the sensed capacitance drops below a predetermined or predeterminable level, thereby indicating that the contact member (40) has reached the stop position, and to provide a corresponding indication for use by a controller in controlling motor-driven retraction of the support member (10) to the retracted position.

The use of a capacitive sensor is just one approach for sensing movement of the contact member from the rearward position to the stop position. In other embodiments, a sensor for sensing such movement and providing an output responsive thereto may comprise a reflective optical sensor, an ultrasound sensor, a linear variable differential transformer sensor, etc.

As may be appreciated, the described operation of syringe plunger positioning apparatus (1) accounts for the above-noted offset distance between the distal end portions of the arm members (60*a*), (60*b*) and the inside surface of the plunger button, as shown in FIG. 4B. In turn, retracted positioning of the plunger button may be completed to yield enhanced plunger positioning and syringe filling accuracy.

Figure 5A:
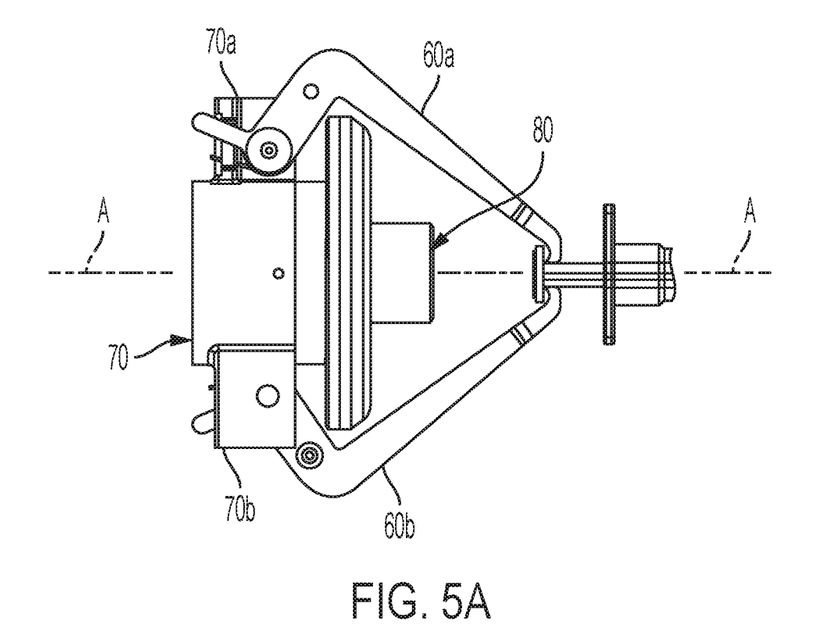
FIGS. 5A and 5B are top views of the syringe plunger positioning apparatus of FIG. 1A employed in conjunction with a syringe having a relatively small plunger button and a syringe having a relatively large plunger button, respectively.
Figure 5B:
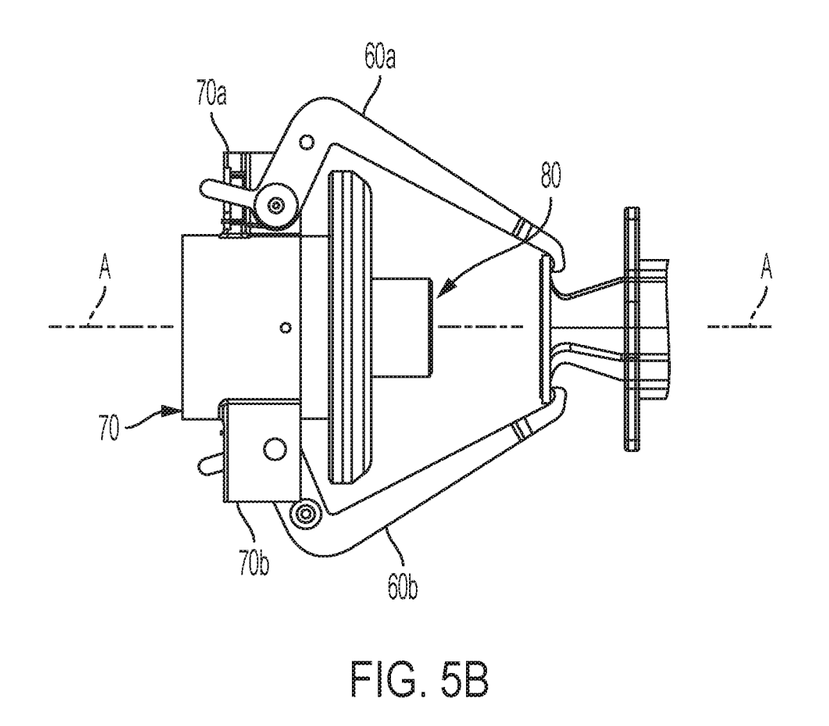

Further, such enhanced accuracy may be realized while accommodating a wide range of plunger button configurations. In that regard, FIGS. 5A and 5B illustrate the engagement of the distal end portions of the arm members (60a), (60b) with a syringe having a relatively small plunger button configuration, and with a syringe having a relatively large plunger button configuration, respectively. As may be appreciated, both syringe button configurations are accommodated by virtue of the configuration, controlled movement, and biasing of the arm members (60a), (60b).

More particularly, and as illustrated in FIGS. 5A and 5B, the arm members (60a), (60b) may each define a U-shaped configuration along a length thereof. In that regard, each of the members may include adjoining first and second portions defining an included angle therebetween. In contemplated arrangements, the included angle may be between about 9° to about 75°.

As further illustrated in FIGS. 5A and 5B, the distal end portions of the arm members (60a), (60b) may each comprise reduced second ends that taper towards first ends of the arm members (60a), (60b). In that regard, the reduced ends may be provided to facilitate non-slip contact engagement with the inside surface of a plunger button of a syringe.

Figure 6:
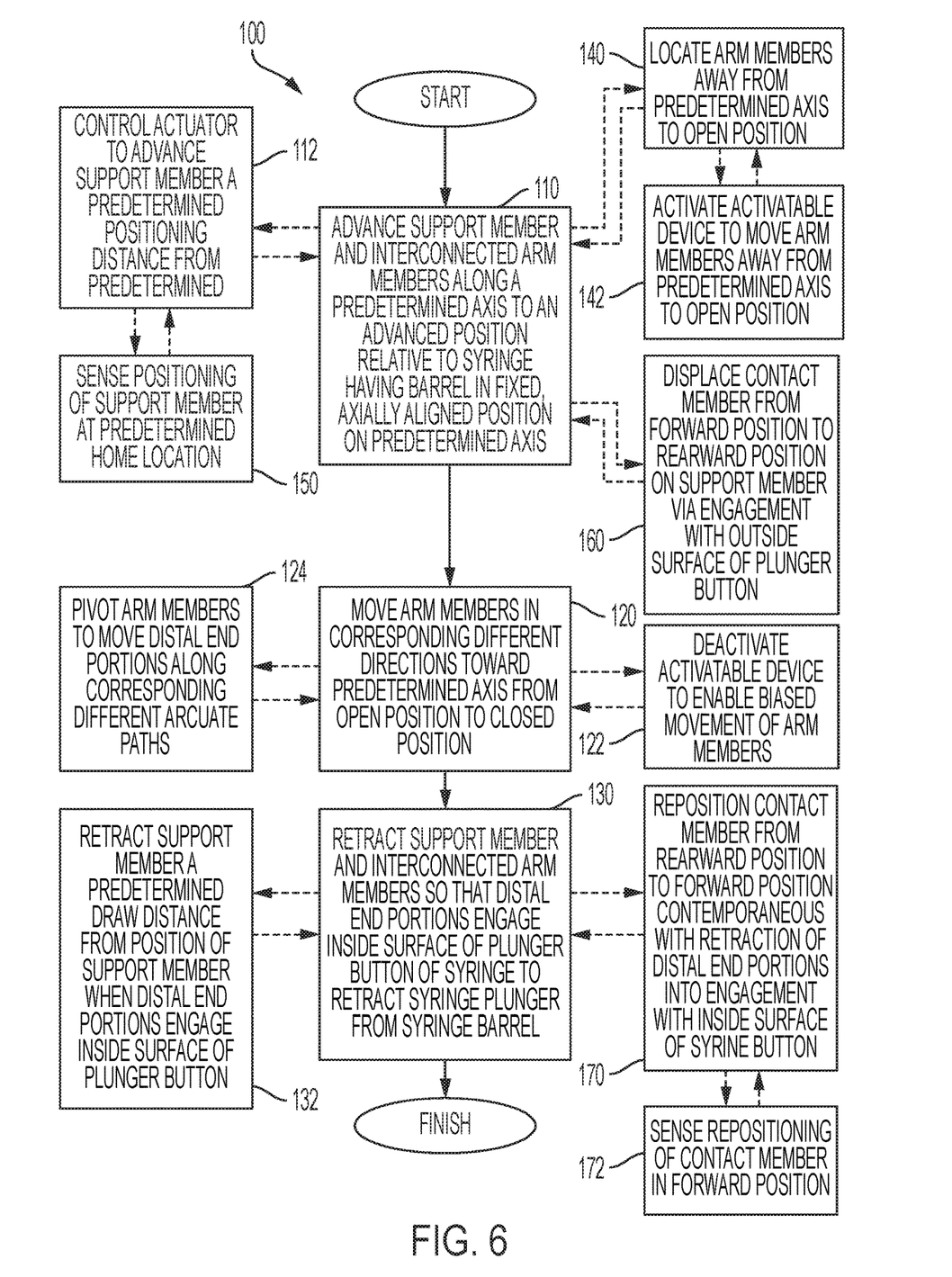
FIG. 6 is a process flow diagram of one embodiment of a syringe plunger positioning method.

Reference is now made to FIG. 6 which illustrates one embodiment of a method for syringe plunger positioning (100). Method embodiment (100) includes advancing a support member and a plurality of arm members interconnected to the support member along a predetermined axis to an advanced position relative to a syringe having a barrel in a fixed, axially aligned position on the predetermined axis (110). The method embodiment (100) further includes moving each of the arm members in corresponding different directions toward the predetermined axis from an open position to a closed position (120), and after the advancing step (110) and moving step (120), retracting the support member and interconnected arm members from the advanced position so that distal end portions of the arm members engage and apply a retraction force to an inside surface of a plunger button of the syringe to retract a plunger from the syringe barrel (130).

In some embodiments, the method embodiment (100) may further comprise locating the arm members in the open position prior to advancement of the support member and arm members to the advanced position (140). In one approach, the arm members may be biased towards the closed position, and the locating step (140) may comprise activating an activatable device to engage and thereby move the arm members away from the predetermined axis to the open position (142). In turn, activation of the activatable device may be maintained during at least a portion of the advancing step (110), and the moving step (120) may include deactivating the activatable device to disengage the activatable device from the plurality of arm members so as to enable biased movement of the arm members to the closed position (122). In some embodiments, the moving step (120) may include pivoting the arm members to move the distal end portions thereof along corresponding different arcuate paths towards the predetermined axis AA (124). Such arcuate paths may be provided to facilitate positioning of the distal end portions about the periphery of a plunger button.

In some implementations, the advancing step (110) may include controlling an actuator (e.g. an electric motor mechanically interconnected to a linear actuator) to advance the support member a predetermined positioning distance along the predetermined axis from a predetermined home location (112). The predetermined positioning distance may be established in relation to a predetermined location range of a button of a plunger of a syringe having a barrel supportably located at a fixed, axially aligned position on the predetermined axis AA. By way of example, such predetermined location range may be based upon positioning of a dispensing end of a given syringe at a predetermined location, or reference datum, on the predetermined axis, and further based upon predetermined data stored at the controller relating to a length of the syringe barrel of the given syringe.

The method embodiment (100) may further comprise sensing the positioning of the support member at the home location and providing a sensor output responsive thereto (150), prior to the controlling step (122). By way of example, the sensor output may be provided to a controller that controls the actuator to advance and retract the actuator along the predetermined axis.

In some embodiments, the retracting step (130) may include retracting the support member a predetermined draw distance from a position of the support member when the distal end portions of the arm members initiate engagement with the inside surface of the plunger button (132). In that regard, the predetermined draw distance may correspond with a desired, predetermined magnitude of syringe filling with a flowable material. By way of example, the desired, predetermined magnitude of syringe filling may correspond with a specific volume of flowable material and/or a specified graduation on a syringe barrel indicative of a corresponding volume of flowable material.

In conjunction with the retracting step (132), method embodiment (100) may comprise displacing a contact member supported by the support member from a forward position to a rearward position, relative to the support member, by engagement of the contact member with an outside surface of the plunger button (160), during an end portion of the advancing step (110). In turn, the method embodiment (100) may further comprise moving the contact member forwardly from the rearward position to a stop position, relative to the support member, contemporaneous with retraction of the distal end portions of the arm members from the advanced position into engagement with the inside surface of the plunger button (170). In some arrangements, the moving step (170) may include applying automatically a biasing force to the contact member (172).

In some implementations, the method embodiment (100) may further comprise sensing the movement of the contact member from the rearward position to the stop position and providing a sensor output responsive thereto (180). In one approach, the sensing step (170) may include sensing an electrical capacitance between a first conductive surface located on and in fixed relation to the support member and a second conductive surface located on and in fixed relation to the contact member, and providing a sensor output indicative of the sensed capacitance. In turn, a method embodiment (100) may further comprise processing the output to determine when a rate of change of the capacitance drops below a predetermined or predeterminable level, whereupon the actuator may be controlled to retract the support member the predetermined draw distance referenced in the retracting step (132).

As may be appreciated, the method embodiment (100) may utilize various features described above in relation to the syringe plunger positioning apparatus (1). Such features may be utilized to augment the described method steps to provide added functionalities.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only preferred embodiment and variants thereof have been shown and described and that all changes and modifications that come within the spirit of the invention are desired to be protected.

What is claimed is:

1. An apparatus for syringe plunger positioning, comprising:
   an actuator to linearly advance and retract a support member along a predetermined axis;
   a plurality of arm members, each interconnected to the support member for movement therewith from an open position to a closed position, and each moveable relative to the support member in corresponding different directions toward the predetermined axis, wherein the actuator is operable to advance the support member to an advanced position for movement of said plurality of arm members in said different corresponding directions towards the predetermined axis from the open position to the closed position, prior to contacting a plunger button of a syringe, and to retract the support member from the advanced position so that distal end portions of each of the plurality of arm members engage an inside surface of the plunger button of the syringe having a barrel located in a fixed, axially aligned position on the predetermined axis.

2. The apparatus of claim 1, further comprising:
   a contact member interconnected to the support member for movement therewith, and located and moveable relative to the support member along the predetermined axis so that, upon said advancement of the support member to said advanced position by said actuator, the contact member is engageable with and displaceable from a forward position to a rearward position along the predetermined axis, relative to the support member, by an outside surface of the plunger button of the syringe having the barrel located in the fixed, axially aligned position on the predetermined axis.

3. The apparatus of claim 2, wherein said contact member is provided so that, upon said retraction of the support member from said advanced position by the actuator said contact member automatically moves from said rearward position to a stop position, relative to the support member, contemporaneous with retraction of said distal end portions of the plurality of arm members into engagement with the inside surface of the plunger button of the syringe, and further comprising:
   a first sensor for sensing said movement of said contact member from said rearward position to said stop position, relative to the support member, and for providing a first sensor output indicative thereof, wherein said first sensor output is employable to control said actuator to retract said support member to a retracted position that is a predetermined draw distance along said predetermined axis from a position of the support member that corresponds with said sensing of the movement of the contact member from said rearward position to said stop position, relative to the support member.

4. The apparatus of claim 3, wherein said predetermined draw distance corresponds with a predetermined magnitude of syringe filling with a flowable material.

5. The apparatus of claim 3, wherein said contact member is biased toward said forward position so that, upon said retraction of the support member from said advanced position by the actuator, said biasing is configured to automatically move the contact member from said rearward position to said stop position, relative to the support member.

6. The apparatus of claim 3, wherein said first sensor is a capacitive sensor comprising:
   a first conductive surface supported by and moveable with said support member; and,
   a second conductive surface supported by and moveable with said contact member, wherein said capacitive sensor is operable to sense an electrical capacitance between said first and second conductive surfaces, and to provide said first sensor output indicative of the sensed capacitance.

7. The apparatus of claim 6, further comprising:
   a processor for processing said first sensor output during movement of said contact member from the rearward position to the stop position to determine when the contact member reaches the stop position, wherein upon a controller is operable to control said actuator to retract said support member said predetermined draw distance to said retracted position.

8. The apparatus of claim 3, wherein said actuator comprises an electric motor, and further comprising:
   a controller operable to automatically control operation of the motor to advance said support member to said advanced position, and to automatically control operation of the motor to retract said support member from said advanced position to said retracted position utilizing said first sensor output.

9. The apparatus of claim 8, wherein said controller is operable to automatically control operation of the motor to retract said support member from said advanced position to said retracted position in a continuous motion.

10. The apparatus of claim 8, wherein said actuator further comprises: a linear actuator extending along said predetermined axis and operatively interconnected to an output shaft of said motor and to said support member for driven movement of said support member along said predetermined axis upon operation of said motor.

11. The apparatus of claim 8, further comprising:
    a second sensor for sensing positioning of the support member in a predetermined home location and for providing second sensor output indicative thereof to said controller, wherein said controller is operable to automatically control said motor to advance said support member a predetermined positioning distance along said predetermined axis from said predetermined home location to said advanced position.

12. The apparatus of claim 11, wherein said plurality of arm members are each moveable so that said corresponding distal end portions follow corresponding different arcuate paths towards said predetermined axis.

13. The apparatus of claim 12, wherein said plurality of arm members are pivotally interconnected to a housing fixedly interconnected to an upstanding portion of said support member.

14. The apparatus of claim 13, wherein said plurality of arm members comprises two arm members disposed for pivotal movement towards and away from said predetermined axis on opposing sides of the predetermined axis and, wherein said two arm members are disposed for said pivotal movement in a common plane comprising said predetermined axis.

15. The apparatus of claim 13, wherein said plurality of arm members are each biased to said closed position relative to said predetermined axis, and further comprising:
    a solenoid having an end portion extending from the housing and selectively displaceable upon activation of said solenoid to engage said plurality of arm members and thereby pivot the plurality of arm members from said closed position to the open position relative to the predetermined axis, wherein the end portion is disc-shaped and has a contact portion that is parallel to corresponding engagement portions of said plurality of arm members when said plurality of arm members are in the open position.

16. The apparatus of claim 15, further comprising:
a controller for automatically controlling activation and deactivation of said solenoid, wherein said solenoid is deactivated when said support member is located in said advanced position, and when the support member is retracted from the advanced position.

17. The apparatus of claim 12, wherein said plurality of arm members each define a U-shaped configuration along a length thereof.

18. The apparatus of claim 17, wherein said plurality of arm members each include first and second portions defining an included angle of between about 9° to about 75° between the first and second portions.

19. The apparatus of claim 17, wherein said distal end portions of said plurality of arm members each comprise reduced ends that taper towards said support member when said plurality of arms are biased to said closed position relative to said predetermined axis.

20. The apparatus of claim 1, wherein said plurality of arm members are moveable for synchronous advancement of said corresponding distal end portions toward said predetermined axis.

* * * * *